United States Patent
Ernst et al.

(10) Patent No.: US 11,008,703 B2
(45) Date of Patent: May 18, 2021

(54) METHOD FOR DETERMINING THE REPLACEMENT STATE OF WEAR OF A ROPE MADE OF A TEXTILE FIBRE MATERIAL

(71) Applicant: TEUFELBERGER FIBER ROPE GMBH, Wels (AT)

(72) Inventors: Björn Ernst, Gmunden (AT); Erich Rührnössl, Haid (AT); Rudolf Kirth, Vöcklabruck (AT); Peter Baldinger, Schwertberg (AT); Robert Traxl, Ebensee (AT); Gunter Kaiser, Thalheim/Wels (AT)

(73) Assignee: TEUFELBERGER FIBER ROPE GMBH, Wels (AT)

( * ) Notice: Subject to any disclaimer, the term of this patent is extended or adjusted under 35 U.S.C. 154(b) by 46 days.

(21) Appl. No.: 16/060,380

(22) PCT Filed: Dec. 14, 2016

(86) PCT No.: PCT/EP2016/080957
§ 371 (c)(1),
(2) Date: Jun. 7, 2018

(87) PCT Pub. No.: WO2017/102821
PCT Pub. Date: Jun. 22, 2017

(65) Prior Publication Data
US 2018/0363241 A1    Dec. 20, 2018

(30) Foreign Application Priority Data

Dec. 16, 2015 (EP) .................................. 15200442

(51) Int. Cl.
| | |
|---|---|
| *G01N 33/36* | (2006.01) |
| *G01N 3/00* | (2006.01) |
| *D07B 1/14* | (2006.01) |
| *B66C 13/16* | (2006.01) |
| *B66D 1/54* | (2006.01) |
| *G01N 3/56* | (2006.01) |
| *B66C 15/00* | (2006.01) |
| *B66C 15/06* | (2006.01) |

(52) U.S. Cl.
CPC .............. *D07B 1/145* (2013.01); *B66C 13/16* (2013.01); *B66C 15/00* (2013.01); *B66C 15/06* (2013.01); *B66D 1/54* (2013.01); *G01N 3/00* (2013.01); *G01N 3/56* (2013.01); *G01N 33/367* (2013.01); *D07B 2205/2014* (2013.01); *D07B 2301/259* (2013.01); *D07B 2301/45* (2013.01); *G01N 2203/0017* (2013.01); *G01N 2203/0023* (2013.01); *G01N 2203/0026* (2013.01); *G01N 2203/028* (2013.01); *G01N 2291/02854* (2013.01); *G01N 2291/2626* (2013.01)

(58) Field of Classification Search
CPC .............. D07B 1/145; D07B 2301/259; D07B 2205/2014; D07B 2301/45; B66C 15/06; B66C 13/16; B66C 13/18; B66C 15/00; G01N 33/367; G01N 2291/2626; G01N 2203/0017; G01N 2203/0026; G01N 2291/02854; G01N 3/56; G01N 2203/0023; G01N 2203/028; G01N 3/08; G01N 3/14; G01N 33/36; B66D 1/54; G01B 7/15; G01B 21/32; G01B 7/02
See application file for complete search history.

(56) References Cited

U.S. PATENT DOCUMENTS

| | | | |
|---|---|---|---|
| 5,461,925 A * | 10/1995 | Nguyen | G01N 3/08 73/160 |
| 2003/0111298 A1 | 6/2003 | Logan et al. | |
| 2005/0226584 A1 | 10/2005 | Williams et al. | |
| 2014/0027401 A1 * | 1/2014 | Ilaka | G01N 3/08 212/276 |
| 2014/0109682 A1 * | 4/2014 | Mupdende | G01N 3/08 73/812 |
| 2018/0011044 A1 * | 1/2018 | Ponniah | G01N 33/365 |
| 2018/0238815 A1 * | 8/2018 | Mupende | B66B 7/1238 |

FOREIGN PATENT DOCUMENTS

| | | |
|---|---|---|
| EP | 1530040 A1 | 5/2005 |
| EP | 1905892 A2 | 4/2008 |
| JP | 2001192183 A | 7/2001 |
| WO | WO2004029343 | 4/2004 |
| WO | WO2015139842 | 9/2015 |

* cited by examiner

*Primary Examiner* — Brandi N Hopkins
(74) *Attorney, Agent, or Firm* — Workman Nydegger

(57) ABSTRACT

The invention relates to a method for determining the replacement state of wear of a rope made of a textile fibre material, wherein, in the course of using the rope, the elongation of the rope is monitored over its entire length and the rope is discarded if the elongation of the rope over the entire length exceeds a predetermined maximum value (%). The method according to the invention is characterized in that also the local elongation of a discrete rope section is monitored and the rope is discarded if the local elongation of the rope section exceeds a predetermined maximum value (%), with the maximum value of the local elongation of the rope section being greater than the maximum value of the elongation of the rope over the entire length.

20 Claims, No Drawings

METHOD FOR DETERMINING THE REPLACEMENT STATE OF WEAR OF A ROPE MADE OF A TEXTILE FIBRE MATERIAL

BACKGROUND

The present invention relates to a method for determining the replacement state of wear of a rope made of a textile fibre material.

Ropes made of a textile fibre material, e.g., synthetic fibre ropes, are used for numerous applications. Especially in the field of materials handling, high-strength fibre ropes are now superior to steel ropes, which previously were used and, respectively, available exclusively, because of several advantages.

During their use, ropes are exposed to various stresses, which, in particular, are mechanical. A person skilled in the art will understand that the "replacement state of wear" ("point of discard") is the point at which the rope can no longer be used or, respectively, can no longer be used to a sufficiently safe extent due to the wear caused by those stresses and, therefore, must be taken out of use.

Of course, the determination of the replacement state of wear is particularly important especially in applications such as, e.g., crane ropes or ropes in lifts.

Various methods are known for detecting the replacement state of wear of a rope made of a textile fibre material.

So far, none of those methods have prevailed on the market. The previously inexistent possibility of safely identifying the replacement state of wear of fibre ropes may be regarded as one of the main reasons as to why, so far, fibre ropes have not yet become accepted for industrial use.

It is inherent to most of the published methods that they detect only one characteristic of the rope at a time (e.g., diameter, elongation or the like). However, since, in most applications, several different damage mechanisms, which influence each other, take effect on a regular basis, such methods are not sufficient for enabling the safe identification and prediction of the replacement state of wear of a fibre rope.

Various methods are known in which one or several additional different fibres (in most cases with a sensor or transfer function) are incorporated into the rope, into the fibre material of the rope, in particular into the load-bearing fibre material, wherein the change in their state is supposed to be indicative of a change in the state of the complete rope assembly.

For example, EP 1 930 497 A describes the use of an indicator fibre which has a lower resistance to abrasion in comparison to the other strands of the rope.

This approach is problematic since the underlying assumption that a single indicator fibre experiences the same strain as the most heavily strained part or section of the rope is not always admissible.

Likewise, methods are known which use the elongation of the rope throughout the service life as an evaluation criterion for the condition of the rope as well as the prediction of the replacement state of wear and determine such in various ways, for example, from EP 0 731 209 A and EP 2 002 051 A. In the latter document, marks are provided on the sheath of a core/sheath rope (e.g., braided rhombi of a differently coloured material), by means of which elongations or twists of the rope can be detected.

From DE 2013 101 326 U1, the use of an electrically conductive sensor thread is known. WO 2003/054290 A1 proposes a ferromagnetic material by means of which it should be possible to identify also local damage to the rope.

Further prior art is known, for example, from US 2003/111298 A1 as well as from US 2005/226584 A1.

Fibre ropes for hoisting applications and on winches (e.g., hoist ropes) are frequently made of high-strength fibre materials (for example, but not exclusively, from UHMWPE, aramid, LCP and/or PBO).

When those materials are used as base materials for the load-bearing elements of the rope (strands), the properties inherent to the materials should be taken into account.

Thus, in particular the creep behaviour of textile fibres is of relevance.

"Creep" is understood to be the irreversible elongation of the material upon application of a load which is lower than the breaking load of the rope over a period of exposure at a certain temperature.

Said creep behaviour is particularly pronounced, for example, in fibres made of UHMWPE (e.g., Dyneema®).

Therefore, in particular the creep behaviour of fibres made of UHMWPE are discussed hereinbelow. However, the explanations apply generally also to other (high-strength or non-high-strength) fibre types.

The fibre data published on UHMWPE clearly show that the creep of UHMWPE fibres, as they are built into ropes, depends on three factors:

1. the tensile stress acting within the material
2. the temperature
3. the duration of exposure (=time)

An increased tensile stress, an increased temperature and an extended duration of exposure will lead, each on its own, to an increased elongation of the material. In this connection, it should be noted that the dependence of the creep rate (=elongation per unit of time) on the tensile stress and the temperature is nonlinear.

Since, in use, the ropes are subjected on a regular basis to unpredictable requirements because of different tensile stresses, temperatures and operating times, they will often fail not with creep as the cause of failure, but due to other dominant damage mechanisms.

Consequently, the ropes have different elongations at the time of the replacement state of wear or, respectively, at the time of failure.

But even if creep is the cause of failure, the ropes have different elongations at the time of the replacement state of wear or, respectively, at the time of failure so that identifying the replacement state of wear based on the elongation of the rope has so far not been possible.

It has been published scientifically that the elongation of UHMWPE fibres as they enter the range of tertiary creep (=rapidly diminishing load-bearing capacity of the fibre due to the rupture of molecular chains) is not constant, but always depends on load, temperature and time. (Vlasblom/Bosman, 2006: Predicting the Creep Lifetime of HMPE Mooring Rope Applications, FIG. 17).

The conclusion drawn from this is that the elongation of the rope up to the replacement state of wear likewise depends on load, temperature and time and is not constant.

In the above-mentioned article by Vlasblom/Bosman, a maximum allowable elongation of the rope over the entire length of 10% is taken as a discard criterion under certain restrictions for standing ropes which are not bent over sheaves during operation. This maximum allowable elongation of the rope is far below the minimum elongation at break of the fibre caused by creep.

For running ropes which are bent over sheaves during operation, such a recommendation does not exist.

Thus, based on the data from literature, a person skilled in the art will currently assume that the following is true:

If creep constitutes the failure mechanism of the fibre, the elongation until break of the fibre is not constant, but always depends on load, temperature and time.

If creep constitutes the failure mechanism of the rope, the elongation until break of the rope is not constant, but always depends on load, temperature and time.

In applications with a non-constant load, temperature and time, the elongation of the fibre or, respectively, the rope is a function of the load spectrum (i.e., the course of load, temperature and time).

The strain history of the fibre/rope thus influences the elongation until break of the fibre/rope.

Thus, in running applications, reaching a certain absolute fibre/rope elongation does not allow a reliable statement about the residual elongation until break of the fibre/rope (as the elongation until break of the fibre/rope is not constant).

Analogously, reaching a certain absolute rope elongation does not allow a reliable statement about the residual elongation until break of the rope and thus the determination of the point in time of the replacement state of wear.

The elongation until break of the rope is different from the elongation until break of the individual fibre. The reason for this is found in the processing of the fibres into the rope (twining, stranding, braiding, twisting, among other things). See Vlasblom/Bosman 2006 FIG. 14.

In addition, with ropes made of different fibre materials A and B, respectively, which each display creep behaviour, it becomes apparent that, from the behaviour (elongation/duration) of the individual fibres A and B, respectively, no analogous conclusion can be drawn to the behaviour of ropes made of the respective fibre material A and B in case of breakage. Hence, for determining the elongation of a rope until break, not only the base material used, but also the construction of the rope would have to be considered.

Thus, the following problems arise:

1. To date, no method for identifying the replacement state of wear is known in which the load-bearing fibre itself provides information about the moment at which the rope is to be discarded.

2. The elongation at break of the fibre is a function of the load spectrum (tensile stress, temperature, time) in a nonlinear way.

3. The elongation at break of a rope constructed from those fibres is a function of the load spectrum (tensile stress, temperature, time) in a nonlinear way.

4. The elongation at break of the rope is different from the elongation at break of the fibre.

BRIEF SUMMARY

Thus, the object consists in providing a method for identifying the replacement state of wear of a rope made, in particular, of high-strength fibre materials such as, e.g., UHMWPE fibres, by means of which the replacement state of wear of the rope can be determined independently of the load history.

Said object is achieved by means of a method for determining the replacement state of wear of a rope made of a textile fibre material, wherein, in the course of using the rope, the elongation of the rope is monitored over its entire length and the rope is discarded if the elongation of the rope over the entire length exceeds a predetermined maximum value (%), which is characterized in that also the local elongation of a discrete rope section is monitored and the rope is discarded if the local elongation of the rope section exceeds a predetermined maximum value (%), with the maximum value of the local elongation of the rope section being greater than the maximum value of the elongation of the rope over the entire length.

DETAILED DESCRIPTION OF THE INVENTION

The term "rope made of a textile fibre material" means that the essential components of the rope, in particular its load-bearing elements, are composed of a textile fibre material such as, e.g., strands of synthetic fibres. The rope according to the invention may also comprise components of other materials such as, e.g., a core of a non-textile material, a sheath of a non-textile material, materials impregnating the rope or rope components or individual non-textile strands with specific functions, for example, for the transmission of electrical signals.

Preferably, the rope is composed of a textile fibre material, both in terms of load-bearing and non-load-bearing components.

In the practice of winch applications, it has been shown that the behaviour of ropes made of a creeping textile fibre material (in particular UHMWPE) deviates from the fibre data:

For example, in experiments on a crane rope test facility, the following is shown (such as described, for example, in WO 2012/146380 A):

1. If a rope made of a textile creeping high-strength fibre material (e.g., UHMWPE) is subjected to constant loads with safety factors 100>Sf>2.8 at non-constant temperatures, the irreversible elongation (creep elongation) of the rope will increase over time.

2. In doing so, each rope section can be subjected to different loads (tractive forces of the rope, number of bending cycles per stroke, loading duration etc.), depending on the application. Depending on the rope section, the rope is thus exposed to different conditions over its rope length.

3. It has been shown that the elongation at failure of the examined textile rope made of UHMWPE lies in a comparatively low value range of approximately 1.8% to 3.8% on a crane rope test facility, as a function of tensile stress, temperature and duration of exposure.

Furthermore, the following is shown in experiments on a continuous bending machine:

4. On single continuous bending machines, as they are currently state of the art in the research of ropes, the elongation at break of an examined textile rope made of UHMWPE lies in a comparatively low value range of approximately 2.5% to 3.1%.

However, it has been shown that the local elongation at failure in small rope sections (herein: the single bending zone) is significantly greater than the elongation at break of the entire rope. The local elongation at failure lies in a range of 10-16%.

This finding forms the basis for the method according to the invention according to which, in addition to monitoring the elongation at break of the entire rope, a monitoring of the elongation at break of small rope sections is used, since those must be monitored far more accurately because of the greater change.

Furthermore, it has been shown that the local elongation at failure of small rope sections is almost independent of the tensile stress and of the temperature and is almost constant. This finding completely contradicts the current scientific consensus which is shared, in particular, by fibre manufacturers and is summarized above.

According to said finding, the elongation at break of small rope sections is thus independent of tensile stress, temperature and duration of exposure, and the rope can therefore be monitored on the basis of maximum absolute elongations which occur locally.

According to the invention, the local elongation of one or in particular also several rope section(s) is thus monitored in addition to the monitoring of the elongation of the rope over its entire length.

Based on the above-described surprising finding, the maximum value to be established for detecting the replacement state of wear may thereby be well above the maximum value for the elongation over the entire length of the rope and, thus, can be detected much more accurately. According to the invention, the rope is discarded also if such a local maximum value is exceeded in a small rope section, even if the maximum value for the elongation over the entire length of the rope has not yet been reached.

The local elongation in (%) to be determined is based on the original length of a rope section having a length of 10 times the lay length of the rope in said rope section.

In a preferred embodiment of the present invention, the maximum value (%) of the local elongation of the discrete rope section is higher than the maximum value (%) of the elongation of the rope over the entire length by a factor of 1.2 to 20, preferably 3.0 to 15.

In this connection, the respective maximum values for the elongation of the rope over the entire length as well as for the maximum allowable elongation of local rope sections are to be established depending on the exact material type for the fibre material used and on the rope structure (lay length, ply yarn twist, etc.).

For example, it has been established for a rope made of a fibre material of aramid that the factor is 1.4. For another rope made of a particular type of UHMWPE (Dyneema®), a factor of 10 has been determined.

Prior to employing the rope in use, those values are to be determined experimentally by means of experiments on a crane rope test facility (e.g., WO 2012/146380A2) as well as by continuous bending tests (such as known from the prior art).

A further preferred embodiment of the method according to the invention is characterized in that the monitored rope is a core/sheath rope.

Ropes made of a textile fibre material, which are provided in a core/sheath structure, are known per se, see, for example, the document US 2005/011344 A1. Such a rope is composed of one or several, for example braided or laid core(s) of a textile fibre material, which is/are surrounded by a textile fibre material as a sheath, which, for example, is braided around it/them.

For the purposes of the present invention, the term "core" hereinafter denotes both a single core and a plurality of cores present in a rope.

In this connection, the monitoring of the elongation of the rope or, respectively, the rope section may occur within the core of the rope. This has the advantage that the elongation of the load-bearing fibre material within the core gives a better indication of the state of the rope.

Likewise or in addition, the monitoring of the elongation of the rope or, respectively, the rope section may occur within the sheath of the rope.

Combinations of those measures are also possible, according to which, for example, the elongation of discrete sections within the core is monitored, whereas the elongation of the total length is monitored on the sheath, and vice versa.

Preferably, a rope section is monitored as a discrete rope section which ends up lying in a bending zone when the rope is used. Especially in such sections, the rope is under particular strain, and, therefore, the monitoring of a local elongation is of great significance.

Particularly preferably, the monitored rope is used as a load rope, in particular with a Koepe-sheave or drum drive. In particular, the method according to the invention is perfectly suitable for determining the replacement state of wear of crane ropes, lift ropes and the like.

The determination of the elongation of the rope or, respectively, the rope section may occur in a manner known per se by means of indicator fibres present within the rope or, respectively, within the core and/or within the sheath of the rope.

Alternatively, non-textile indicator materials, e.g., ferromagnetic indicators, may be used as well.

The method according to the invention is preferably applied to a rope the load-bearing fibre material of which consists of high-strength synthetic fibres.

For the purposes of the present invention, fibres having a tensile strength of at least 14 cN/dtex, preferably a tensile strength of more than 24 cN/dtex, particularly preferably of more than 30 cN/dtex, are understood to be "high-strength". UHMWPE fibres (Dyneema®), aramid fibres, LCP fibres and PBO fibres are, for example, known as high-strength fibre types having appropriate tensile strengths. Preferably, the high-strength synthetic fibres are UHMWPE fibres at least partially, particularly preferably in their entirety.

A "load-bearing fibre material" is understood to be the part of the fibre material of the rope which contributes to the absorption of the tensile forces arising during the use of the rope.

The method according to the invention is preferably performed on a rope
a) the load-bearing fibre material of which consists of high-strength synthetic fibres
b) which is provided in the form of a spiral strand rope
c) which comprises at least two, preferably at least three concentric load-bearing strand layers
d) wherein the individual strands of the strand layers are movable against each other
e) wherein the degree of filling with a textile fibre material is ≥75%, preferably ≥85%, and
e) wherein the outermost layer of the rope has a coefficient of friction μ in comparison to steel of μ<0.15.

Such a rope is described in PCT/EP2015/075032 (not pre-published), the disclosure of which is herewith referred to.

EXAMPLES

Example 1

Testing of a rope having the above-indicated features a) to e) and made of the high-strength textile fibre material UHMWPE:

The monitoring of a discrete rope section which ended up lying in a bending zone revealed an elongation of 15.5% throughout the service life of the rope.

The monitoring of the entire rope revealed an elongation of 2.9% throughout the service life of the rope.

Thus, the result is a factor of 15.5/2.9=5.35 by which the elongation of the discrete rope section will be higher than that of the rope over the entire length at the end of the service life.

For determining the replacement state of wear of such a rope, it has correspondingly been established as a maximum value for the local elongation that, among other things, the rope has to be discarded if the local elongation of a discrete rope section exceeds a value of 6.0% or, respectively, if the elongation of the entire rope exceeds 1.6%.

Example 2

Testing of a rope having the above-indicated features a) to e) and made of the high-strength textile fibre material aramid:

The monitoring of a discrete rope section which ended up lying in a bending zone revealed an elongation of 5.2% throughout the service life of the rope.

The monitoring of the entire rope revealed an elongation of 3.0% throughout the service life of the rope.

Thus, the result is a factor of 5.2/3.0=1.73 by which the local elongation of the discrete rope section will be higher than that of the rope over the entire length at the end of the service life.

For determining the replacement state of wear of such a rope, it has correspondingly been established as a maximum value for the local elongation that, among other things, the rope has to be discarded if the local elongation of a discrete rope section exceeds a value of 5.0% or, respectively, if the elongation of the entire rope exceeds 2.9%.

The invention claimed is:

1. A method for determining a replacement state of wear of a rope made of a textile fibre material, comprising:
   monitoring, during use of the rope, an elongation of the rope over its entire length and discarding the rope if the elongation of the rope over its entire length exceeds a first predetermined maximum value (%), and
   also monitoring local elongation of a discrete rope section and discarding the rope if the local elongation of the discrete rope section exceeds a second predetermined maximum value (%),
   wherein the second predetermined maximum value (%) of the local elongation of the discrete rope section is greater than the first predetermined maximum value (%) of the elongation of the rope over its entire length, and
   wherein the first predetermined maximum value (%) of the elongation of the rope over its entire length and the second predetermined maximum value (%) of the local elongation of the discrete rope section are established based on a type of textile fibre material used and a structure of the rope.

2. A method according to claim 1, wherein the second predetermined maximum value (%) of the local elongation of the discrete rope section is higher than the first predetermined maximum value (%) of the elongation of the rope over its entire length by a factor ranging from 1.2 to 20.

3. A method according to claim 2, wherein the second predetermined maximum value (%) of the local elongation of the discrete rope section is higher than the first predetermined maximum value (%) of the elongation of the rope over the entire length by a factor ranging from 3.0 to 15.

4. A method according to claim 1, wherein the method is applied to a rope which is a core/sheath rope.

5. A method according to claim 4, wherein the monitoring of the elongation of the rope over its entire length or, respectively, the discrete rope section occurs within a core of the rope.

6. A method according to claim 4, wherein the monitoring of the elongation of the rope over its entire length or, respectively, the discrete rope section occurs within a sheath of the rope.

7. A method according to claim 1, the method comprising monitoring a rope section as a discrete rope section which ends up lying in a bending zone when the rope is used.

8. A method according to claim 1, wherein the rope is a load rope.

9. A method according to claim 8, wherein the use of the rope is with a Koepe-sheave or drum drive.

10. A method according to claim 1, wherein the determination of the elongation of the rope over its entire length or, respectively, the discrete rope section occurs by means of indicator fibres present within the rope.

11. A method according to claim 1, wherein the rope to which the method is applied consists essentially of the textile fibre material, both in terms of load-bearing and non-load-bearing components.

12. A method according to claim 1, wherein a load-bearing fibre material of the rope to which the method is applied consists of high-strength synthetic fibres.

13. A method according to claim 12, wherein the high-strength synthetic fibres are at least partially UHMWPE fibres.

14. A method according to claim 12, wherein the rope on which the method is performed has the following properties:
   a) the load-bearing fibre material consists of high-strength synthetic fibres,
   b) the rope is provided in the form of a spiral strand rope,
   c) the rope comprises at least two concentric load-bearing strand layers,
   d) the individual strands of the strand layers are movable against each other,
   e) the rope has a degree of filling with a textile fibre material of ≥75%, and
   e) the outermost layer of the rope has a coefficient of friction $\mu$, in comparison to steel of $\mu<0.15$.

15. A method according to claim 14, wherein the degree of filling with a textile fibre material is ≥85%.

16. A method according to claim 14, wherein the rope comprises at least three concentric load-bearing strand layers.

17. A method for determining a replacement state of wear of a rope made of a textile fibre material, comprising:
   monitoring, during use of the rope, an elongation of the rope over its entire length and discarding the rope if the elongation of the rope over its entire length exceeds a first predetermined maximum value (%), and
   also monitoring local elongation of a discrete rope section and discarding the rope if the local elongation of the discrete rope section exceeds a second predetermined maximum value (%),
   wherein the second predetermined maximum value (%) of the local elongation of the discrete rope section is greater than the first predetermined maximum value (%) of the elongation of the rope over its entire length; and
   wherein the second predetermined maximum value (%) of the local elongation of the discrete rope section exceeds the first predetermined maximum value (%) of the elongation of the rope over its entire length by a factor ranging from 1.2 to 20.

18. A method for determining a replacement state of wear of a rope made of a textile fibre material, comprising:
   monitoring, during use of the rope, an elongation of the rope over its entire length and discarding the rope if the elongation of the rope over its entire length exceeds a first predetermined maximum value (%), and also monitoring local elongation of a discrete rope section and discarding the rope if the local elongation of the discrete rope section exceeds a second predetermined maximum value (%), wherein the second predetermined maximum value (%) of the local elongation of the discrete rope section is greater than the first predetermined maximum value (%) of the elongation of the rope over its entire length; and wherein the discrete rope section ends up lying in a bending zone when the rope is used.

19. A method according to claim 18, wherein the second predetermined maximum value (%) of the local elongation of the discrete rope section exceeds the first predetermined maximum value (%) of the elongation of the rope over the entire length by a factor ranging from 1.2 to 20.

20. A method according to claim 18, wherein the second predetermined maximum value (%) of the local elongation of the discrete rope section exceeds the first predetermined maximum value (%) of the elongation of the rope over the entire length by a factor ranging from 3.0 to 15.

* * * * *